(12) United States Patent
Constantz et al.

(10) Patent No.: US 7,261,718 B2
(45) Date of Patent: *Aug. 28, 2007

(54) USE OF VIBRATION WITH POLYMERIC BONE CEMENTS

(75) Inventors: Brent R. Constantz, Cupertino, CA (US); David Delaney, Scotts Valley, CA (US); Duran Yetkinler, Cupertino, CA (US)

(73) Assignee: Skeletal Kinetics LLC, Cupertino, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/900,019

(22) Filed: Jul. 26, 2004

(65) Prior Publication Data

US 2005/0070914 A1     Mar. 31, 2005

Related U.S. Application Data

(63) Continuation-in-part of application No. 10/797,907, filed on Mar. 9, 2004, which is a continuation-in-part of application No. 10/661,356, filed on Sep. 11, 2003.

(51) Int. Cl.
*A61B 17/58* (2006.01)
*A61F 2/00* (2006.01)

(52) U.S. Cl. ..................................... 606/92

(58) Field of Classification Search ............. 606/86, 606/92, 93, 94, 95, 169, 170, 171; 623/23.61, 623/23.62; 433/86; 601/2–4; 604/22, 82–92, 604/187; 366/110, 112, 114; 222/161, 196

See application file for complete search history.

(56) References Cited

U.S. PATENT DOCUMENTS

| | | | |
|---|---|---|---|
| 4,160,012 A | 7/1979 | Ono et al. | |
| 4,161,511 A | 7/1979 | Shiraki et al. | |
| 4,429,691 A | 2/1984 | Niwa et al. | |
| 4,463,875 A * | 8/1984 | Tepic | 222/82 |
| 4,497,075 A | 2/1985 | Niwa et al. | |
| 4,787,751 A * | 11/1988 | Bakels | 366/110 |
| 4,990,163 A | 2/1991 | Ducheyne et al. | |
| 5,244,933 A * | 9/1993 | Eidenbenz et al. | 522/3 |

(Continued)

FOREIGN PATENT DOCUMENTS

DE     100 57 616 A1    11/2000

OTHER PUBLICATIONS

Baroud et al. "Influence of Oscillatory Mixing on the Injectability of Three Acrylic and Two Calcium-Phosphate Bone Cements for Vertebroplasty" (2004) *Journal of Biomedical Materials Research—Part B* 68B(1)105-111.

*Primary Examiner*—Anuradha Ramana
(74) *Attorney, Agent, or Firm*—Bret E. Field; Bozicevic, Field & Francis, LLP (57) ABSTRACT

Methods of employing bone defect filling, e.g., polymeric bone cements, are provided. A feature of the subject methods is that vibration is employed in conjunction with the use of the cement, e.g., in preparation of the cement, in preparation of the target site, in delivery of the cement to the target site, and/or following delivery of the cement to the target site. Also provided are devices, systems and kits that find use in practicing the subject methods. The subject methods, devices and systems find use in a variety of different applications.

10 Claims, 5 Drawing Sheets

U.S. PATENT DOCUMENTS

| | | |
|---|---|---|
| 5,281,265 A | 1/1994 | Liu |
| 5,304,577 A * | 4/1994 | Nagata et al. ............... 524/417 |
| 5,525,148 A | 6/1996 | Chow et al. |
| 5,545,254 A | 8/1996 | Chow et al. |
| 5,580,623 A | 12/1996 | Fulmer et al. |
| 5,639,238 A * | 6/1997 | Fishburne, Jr. ............. 433/215 |
| 5,679,294 A | 10/1997 | Umezu et al. |
| 5,695,729 A | 12/1997 | Chow et al. |
| 5,697,981 A | 12/1997 | Ison et al. |
| 5,900,254 A | 5/1999 | Constantz |
| 5,954,867 A | 9/1999 | Chow et al. |
| 5,962,028 A | 10/1999 | Constantz |
| 5,968,253 A | 10/1999 | Poser et al. |
| 5,976,105 A * | 11/1999 | Marcove et al. ............ 604/500 |
| 5,976,234 A | 11/1999 | Chow et al. |
| 5,997,624 A | 12/1999 | Chow et al. |
| 6,005,162 A | 12/1999 | Constantz |
| 6,027,742 A | 2/2000 | Lee et al. |
| 6,139,320 A * | 10/2000 | Hahn ......................... 433/119 |
| 6,139,578 A | 10/2000 | Lee et al. |
| 6,149,655 A * | 11/2000 | Constantz et al. ............ 606/94 |
| 6,224,635 B1 * | 5/2001 | Ricci et al. ............... 623/23.62 |
| 6,273,916 B1 * | 8/2001 | Murphy .................. 623/23.62 |
| 6,340,299 B1 * | 1/2002 | Saito ........................... 433/80 |
| 6,375,935 B1 | 4/2002 | Constantz |
| 6,551,337 B1 * | 4/2003 | Rabiner et al. ............. 606/169 |
| 6,593,394 B1 * | 7/2003 | Li et al. .................... 523/113 |
| 6,620,162 B2 * | 9/2003 | Kuslich et al. ............... 606/53 |
| 6,733,451 B2 * | 5/2004 | Rabiner et al. ............. 600/439 |
| 6,808,561 B2 * | 10/2004 | Genge et al. ............... 106/690 |
| 6,832,988 B2 * | 12/2004 | Sproul ....................... 600/459 |
| 2002/0155167 A1 | 10/2002 | Lee et al. |
| 2002/0183851 A1 * | 12/2002 | Spiegelberg et al. ..... 623/22.12 |
| 2003/0199615 A1 | 10/2003 | Chaput et al. |
| 2004/0024410 A1 | 2/2004 | Olson, Jr. et al. |
| 2004/0076685 A1 | 4/2004 | Tas |

* cited by examiner

USE OF VIBRATION WITH POLYMERIC BONE CEMENTS

CROSS-REFERENCE TO RELATED APPLICATIONS

This application is a continuation-in-part of application Ser. No. 10/797,907 filed on Mar. 9, 2004; which application is a continuation-in-part of application Ser. No. 10/661,356 filed Sep. 11, 2003; the disclosures of which are herein incorporated by reference.

INTRODUCTION

Background

Orthopedic/bone defect filling cements find use in a variety of different applications, including orthopedic and dental applications. A variety of different orthopedic cements have been developed to date, where such cements include both polymeric based cements, such as PMMA, as well as mineral based cements, e.g., calcium and/or phosphate containing cements. As the field matures, ever more chemical formulations and applications are being developed in which orthopedic cements find use.

While the field of orthopedic/bone defect filling cements has progressed greatly, there continues to be a need for improvements in this area. Where the target bone site is a porous cancellous structure, e.g., as may be encountered in a reduced fracture or inside a compromised vertebral body, one approach is to deliver the cement under high pressure, so that it adequately penetrates the cancellous bone tissue. However, a disadvantage of high-pressure delivery methods is that they can result in penetration beyond the site of interest, and delivery may be hard to control, such that even when the pressure source is removed, cement still penetrates the tissue, perhaps to undesirable areas and/or causing undesirable side effects. Specifically, pressurization of cement in the body often causes emboli of cement or fat which can result in death of the patient or other adverse events.

An alternative to delivery under pressure is to remove the cancellous tissue from the target site to produce a true void space into which the cement composition may be introduced. In certain embodiments, a void space may be produced by introducing a balloon into the target site and expanding the balloon in a manner that compresses the cancellous tissue and results in the production of a void space at the target site. However, there are disadvantages to this approach as well, such as the loss of cancellous tissue. Furthermore, the expansion of the balloon can cause fat emboli that can result in patient death or adverse events.

As such, there continues to be an interest in the development of new protocols and devices for use in applications where such cements are employed.

Literature of Interest

United States patents of interest include: U.S. Pat. Nos. 6,375,935; 6,139,578; 6,027,742; 6,005,162; 5,997,624; 5,976,234; 5,968,253; 5,962,028; 5,954,867; 5,900,254; 5,697,981; 5,695,729; 5,679,294; 5,580,623; 5,545,254; 5,525,148; 5,281,265; 4,990,163; 4,497,075; 4,429,691; 4,161,511 and 4,160,012. Also of interest is published U.S. application Ser. No. 2004/0024410 A1 and Baroud et al., "Influence of Oscillatory Mixing on the Injectability of Three Acrylic and Two Calcium-Phosphate Bone Cements for Vertebroplasty," J. Biomedical Materials Research, Part B-Applied Biomaterials; (Jan. 15, 2004); v. 68B, no. 1, p. 105-111.

SUMMARY OF THE INVENTION

Methods of employing bone defect filling, e.g., polymeric bone cements, are provided. A feature of the subject methods is that vibration is employed in conjunction with the use of the cement, e.g., in preparation of the cement, in preparation of the target site, in delivery of the cement to the target site, and/or following delivery of the cement to the target site. Also provided are devices, systems and kits that find use in practicing the subject methods. The subject methods, devices and systems find use in a variety of different applications, including vertebroplasty applications.

BRIEF DESCRIPTION OF THE FIGURES

FIGS. 1 to 6D provide various views of a pneumatically driven needle vibrating device that may be employed in certain embodiments of the subject invention, e.g., where vibration is employed in conjunction with delivery of a cement to a target bone site.

DESCRIPTION OF THE SPECIFIC EMBODIMENTS

Methods of employing bone defect filling, e.g., polymeric bone cements, are provided. A feature of the subject methods is that vibration is employed in conjunction with the use of the cement, e.g., in preparation of the cement, in preparation of the target site, in delivery of the cement to the target site, and/or following delivery of the cement to the target site. Also provided are devices, systems and kits that find use in practicing the subject methods. The subject methods, devices and systems find use in a variety of different applications, including vertebroplasty applications.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

It must be noted that, as used in this specification and the appended claims, the singular forms "a," "an" and "the" include plural reference unless the context clearly dictates otherwise. Unless defined otherwise all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

Where a range of values is provided, it is understood that each intervening value, to the tenth of the unit of the lower limit, unless the context clearly dictates otherwise, between the upper and lower limit of that range and any other stated or intervening value in that stated range, is encompassed within the invention. The upper and lower limits of these smaller ranges may independently be included in the smaller ranges, and such embodiments are also encompassed within the invention, subject to any specifically excluded limit in the stated range. Where the stated range includes one or both of the limits, ranges excluding either or both of those included limits are also included in the invention.

All publications mentioned herein are incorporated herein by reference for the purpose of describing and disclosing components that are described in the publications that might be used in connection with the presently described invention.

In further describing the subject invention, the subject methods will be described first, as well as representative utilities thereof, followed by a review of representative devices, systems and kits that may be used therein.

Methods

As summarized above, the subject methods are methods of using a bone cement, and particularly a polymeric bone cement. A feature of the subject methods is that the cement employed in the methods is employed in conjunction with vibration. By "in conjunction with vibration" is meant that vibratory force is used at some point during the application or protocol in which the orthopedic cement is being used. Put another way, in a given protocol where a cement is used, the protocol is a method according to the present invention if vibration is used at some point during the protocol, e.g., during preparation and/or delivery of the cement to a target bone site, during preparation of the target bone site, following delivery of the composition to a target bone site, etc.

The term vibration is used to refer to a vibratory or oscillating force that is applied to an object, where the nature of the vibratory force and object to which it is applied may vary depending on the particular embodiment of the subject invention. The force may be applied to a target object, e.g., cement, bone defect site, etc., in a variety of different ways. For example, the force may be applied to the object using a mechanical application element, a sonic application element, etc., as described in greater detail below. Accordingly, representative vibratory forces include sonic forces, mechanical forces, etc.

The vibratory force may be characterized in terms of frequency, such as cycles per second (Hertz or Hz), where in certain embodiments the vibratory force applied to an object during the subject methods may have a frequency that ranges from about 0.1 to about 100,000 Hz or higher, including from about 5.0 to about 100,000 Hz or higher, e.g., from about 5.0 to about 50,000 Hz or higher, such as from about 10 to about 35,000 Hz, including from about 20 to about 20,000 Hz. In certain embodiments, the vibratory force has a frequency that is sufficient to provide for the desired outcome, e.g., full delivery of the cement without application of significant backforce (as described in greater detail below) but does not exceed about 10,000 Hz, and in certain embodiments does not exceed about 5000 Hz, and in certain embodiments does not exceed about 1000 Hz. For example, where the vibratory force applied to an object during the subject methods is a sonic force, the force may be infrasonic or ultrasonic, or in the audible range. The vibratory force may also be characterized in terms of its amplitude or magnitude of vibration. By "amplitude" is meant the movement in any direction. In representative embodiments, the amplitude of the applied vibratory force will range from about 1 Angstrom to about 2 mm, such as from about 1 to about 500 microns, including from about 10 to 100 microns. In certain embodiments, the amplitude of the applied vibratory force will range from about 1 Angstrom to about 1 mm, such as from about 1 to about 100 microns, including from about 10 to 50 microns. Depending on the application and desired nature of the vibratory force, the direction or orientation of the vibration may vary greatly, where representative orientations include, but are not limited to: circular, unidirectional, random, etc. In some instance, the vibration parameters, e.g., frequency and/or amplitude, may be varied over the course or duration of the vibration usage, as may be desired depending on the particular application being performed.

Pursuant to the invention, vibration may be employed at one or more points during a given orthopedic cement protocol. Typically, orthopedic cement protocols at least include: cement preparation, target site preparation, cement delivery to a target site; and optionally post delivery cement modification. Representative points at which vibration may be employed include, but are not limited to: cement preparation; target site preparation; cement delivery to a target site; and post delivery modification of the delivered cement. Each of these different representative times or points at which vibration may be employed is now reviewed separately in greater detail.

In certain embodiments of the subject invention, vibration is used in conjunction with at least the preparation of a polymeric bone cement. By used in conjunction with the preparation of a polymeric bone cement is meant that vibration is employed at some point during the period in which the cement precursors of the cement, e.g., liquid and solid reagents or cement components, are combined to produce a flowable cement product composition. In certain embodiments of the subject invention, vibration is employed by applying a vibratory force, e.g., sonic or mechanical, to the precursors of the flowable composition, e.g., during mixing of the precursors. For example, in certain representative embodiments, vibration may be applied to the container or vessel in which the flowable cement composition is prepared, and thereby applied to the flowable cement composition as it is being prepared.

In certain of these representative embodiments, the vibratory force that is applied to the cement may have a frequency ranging from about 0.1 Hz to about 100,000 Hz, such as from about 5 Hz to about 50,000 Hz, including from about 100 Hz to about 5000 Hz, and an amplitude ranging from about 1 angstrom to about 5 mm, such as from about 1 micron to about 1 mm, including from about 10 micron to about 500 micron. Also of interest are the ranges provided above.

The vibratory force may be applied to the cement components for the duration of the preparatory time or for a portion thereof, e.g., while the initial components are combined, while additives are combined with the product of mixing of the initial components, etc. In certain representative embodiments, vibration is applied for a duration ranging from about 1 sec to about 10 minutes, such as from about 10 sec to about 5 minutes, including from about 15 sec to about 1 minutes and in certain embodiments the vibration is applied for a duration ranging from about 1 sec to about 5 minutes, such as from about 10 sec to about 1 minutes, including from about 15 sec to about 30 sec.

In certain embodiments, vibration is employed in conjunction with at least preparation of the target bone site. In the subject methods, the target bone site may be any of a variety of different bone sites. In representative embodiments, the target bone site is an interior target bone site, e.g., an interior region of a bone, as a cancellous domain bounded by cortical walls. In representative embodiments, the target bone site is made up of cancellous tissue, into which it is desired to penetrate the orthopedic cement to produce a cancellous bone/cement composite structure. Representative cancellous bone target sites of interest include, but are not limited to, those found in: vertebral body sites, femur sites, proximal humerus sites, tibial plateau sites, calcaneous sites, distal radius sites, and the like.

In these embodiments, vibration may be applied to the target bone site using any convenient protocol, depending on the desired outcome of the use vibration in target bone site preparation. For example, in certain embodiments, preparation of the target bone site may include removal of marrow an other materials from the bone site, e.g., the methods may include a marrow or hematoma removal step, where material, e.g., marrow, hematoma, at the target site is removed, e.g., before and/or during delivery of the cement composition, so as to further enhance penetration of the cement into the target site. For example, the marrow may be removed by aspiration from the target bone site. More specifically, marrow may be aspirated from one side of the target site before or as cement is introduced into the other side. In these embodiments, a vibratory force may be applied to the target bone site to enhance the rate and/or efficiency of marrow, e.g., fatty marrow, removal.

In certain of these representative embodiments, the vibratory force that is applied to the target bone site may have a frequency ranging from about 1 Hz to about 100,000 Hz, such as from about 10 Hz to about 10,000 Hz, including from about 100 Hz to about 1000 Hz, and an amplitude ranging from about 1 Angstrom to about 5 mm, such as from about 1 micron to about 100 micron, including from about 5 micron to about 50 micron. In certain representative embodiments, vibration is applied for a duration ranging from about 0.1 sec to about 20 minutes, such as from about 1 sec to about 10 minutes, including from about 10 second to about 5 minutes. Also of interest are the ranges provided above.

In certain embodiments, vibration is employed in conjunction with delivery of the cement to a target site. In other words, a vibratory force is applied to the cement composition during delivery to the target site, such as a target bone site. Put another way, the cement composition is vibrated as it is being delivered to the target bone site.

The cement composition may be vibrated using any convenient protocol. For example, in certain embodiments, a vibratory force may be applied to the target bone site as the cement is being delivered to the target bone site, thereby vibrating the cement as it is delivered to the target bone site. In yet other representative embodiments, the cement is vibrated by applying vibratory force to a cement delivery element, e.g., needle, which is conveying the cement to the target bone site. In yet other embodiments, the vibratory force may be applied directly to the cement during delivery of the cement by a vibratory element distinct from the delivery means, which element is contacted with the cement during delivery in a manner sufficient to impart the desired vibratory force to the cement during delivery.

In representative embodiments, the amount of vibratory force that is applied to the cement, e.g., through application to the delivery element, is typically sufficient to provide for highly controlled penetration of the cement through cancellous bone tissue. By "highly controlled penetration" is meant penetration of the cement through cancellous bone tissue in manner that can be stopped at substantially the same time as cessation of vibration, such that when vibration stops, the cement no longer moves further into the cancellous tissue, and any movement of the cement into the cancellous tissues continues for no more than about 5 seconds, such as no more than about 1 to about 3 seconds.

Where the vibratory force is applied to the cement by applying it to a delivery element for the cement, the delivery element is, in many embodiments, vibrated in the range of about 1 to 100,000 Hz, such as from about 10 to 10,000 vpm, including from about 100 to about 1,000 Hz, and with a force that moves the delivery element a distance in magnitude in either direction of from about 1 Angstrom to about 5.0 mm, such as from about 1 micron to about 100 micron, such as from 5 micron to 50 micron. Also of interest are the ranges provided above.

A feature of certain embodiments of the subject methods of certain of these embodiments is that the cement is delivered in manner that provides for highly controlled penetration without the use of significant back-pressure on the cement. As such, any pressure applied to the cement during delivery does not exceed about 100 psi, and is between about 1 and 100 psi in certain embodiments. In certain of these embodiments, a negative pressure may be present at the target delivery site, which negative pressure enhances entry of the cement composition to the target site. The negative pressure may be produced using any convenient protocol, e.g., the target site preparation protocol described above. Where a negative pressure is present at the target delivery site, the negative pressure may range from about 1 to about 1000 psi, including from about 10 to about 100 psi.

In certain embodiments, a cement is employed in conjunction with hardware to achieve what is known in the art as composite fixation. In composition fixation, the cement may be employed with one or more types of hardware, e.g., screws, plates, wires, etc. In such embodiments, vibration may be applied to the cement during delivery to achieve a superior composite fixation, e.g., in terms of better interface between the cement and hardware components of the composite fixation structure. In many embodiments, the hardware component(s) is delivered/positioned first, followed by delivery of the cement component, which cement component is delivered in conjunction with vibration according to the subject methods.

In certain embodiments, composite fixation may employ the use of what is known in the art as cannulated screws, i.e., screws with hollow centers which have entry and exit ports through which material can be introduced and removed from the hollow center of the screw. In these embodiments, the screw(s) may be placed or positioned in the subject first, e.g., by delivery over a guidewire, according to methods known in the art. Following placement of the screw, the cement is delivered to the site, e.g., through the screw, in conjunction with vibration, where the vibratory force may be applied to the cement itself, a delivery device thereof, and/or the cannulated screw, etc.

In certain embodiments, vibration may be employed in conjunction with post delivery cement modification, e.g., to modulate (for example enhance or impede) the rate of setting of the cement, as desired for a particular application. By selecting the appropriate type, duration and timing of vibratory force, the rate of setting of the cement can be modulated, e.g., increased or decreased, as desired. For example, in certain embodiments, following application or placement of an amount of a cement composition to a target bone site, it may be desirable to decrease or slow the rate at which the cement sets or hardens. For example, a vibratory force may be applied to the cement composition placed or positioned at the target bone site, e.g., to slow cement setting and provide longer time to shape or model the positioned cement composition. For example, in certain embodiments, the cement composition, following placement, may initially set into a first configuration. A vibratory force may be applied to the cement in this first configuration in order to modify it to a second, more desirable configuration. In this manner, the configuration or shape of the positioned or placed cement composition may be fined tuned or tailored to achieve optimal results in a given application. In yet other embodiments, vibration may be applied to further assist the cement in penetrating into space adjacent to the direct site of introduction, e.g., through the cancellous structure of a vertebral body beyond the exact site of implantation or delivery.

In these embodiments where it is desired to slow or impede the rate of cement setting, e.g., by at least about 2-fold, such as by at least about 5-fold, including by at least about 10-fold, the vibratory force that is applied to the delivered cement composition may have a frequency ranging from about 1 to about 100,000 Hz, such as from about 10 to about 10,000 Hz, including from about 100 Hz to about 1000 Hz, and an amplitude ranging from about 1 Angstrom to about 5 mm, such as from about 1 micron to about 100 micron, including from about 5 micron to about 50 micron. In certain representative embodiments, vibration is applied for a duration ranging from about 0.1 sec to about 10 minutes, such as from about 1 sec to about 5 minutes, including from about 10 sec to about 1 minute. Also of interest are the ranges provided above.

In yet other embodiments, a vibratory force is applied that enhances or accelerates the rate of setting of the cement, e.g., by at least about 2-fold, such as by at least about 5-fold, including by at least about 10-fold. In certain of these representative embodiments, the vibratory force that is applied to the delivered cement may have a frequency ranging from about 1 to about 100,000 Hz, such as from about 10 Hz to about 10,000 Hz, including from about 100 Hz to about 1000 Hz, and an amplitude ranging from about 1 Angstrom to about 5 mm, such as from about 1 micron to about 100 micron, including from about 5 micron to about 50 micron. In certain representative embodiments, vibration is applied for a duration ranging from about 0.1 sec to about 10 minutes, such as from about 1 sec to about 5 minute, including from about 10 sec to about 1 minute.

As summarized above, the present invention is directed to the delivery to a target bone site of a polymeric bone cement composition in conjunction with vibration. The bone cements that are delivered according to the subject invention are polymeric materials which may include one or more different types of polymers that, in preparation, undergo a chemical reaction, e.g., a polymerization and/or cross-linking reaction, to produce a final product. The bone cements are, in representative embodiments, prepared by combining a liquid monomer and a powdered copolymer, such as methyl methacrylate and polymethyl methacrylate or methyl methacrylate styrene. As used herein, the terms "(meth) acrylate" and "poly(meth)acrylate" include the monomers and polymers, respectively, of methacrylic acid esters and acrylic acid esters, and the polymers also include the co-polymers of the compounds named.

In representative embodiments, the subject bone cement composition includes a solid finely divided powdery or granular polymer component and a liquid reactive or polymerizable, e.g., monomer, component that is also a solvent or swelling agent for the polymer component. The polymer and monomer components can be based on the acrylic, e.g., (meth)acrylate system, however, other polymeric systems can also be used. For convenience, the cement system may at times be broadly referred to as an acrylic polymer, or as based on PMMA (polymethylmethacrylate), a representative polymer component. While the invention is described herein in terms of a representative embodiment, i.e., bone cement, it is to be understood that the invention is also directed to dental/tooth cements.

More generally, the polymer component of the composition can be any methyl(meth)acrylate polymer such as methyl(meth)acrylate homopolymers and copolymers of methyl(meth)acrylate with alpha, beta-ethylenically unsaturated compounds such as vinyl acetate, alkyl (e.g., $C_2$-$C_6$) (meth)acrylates and multi-functional acrylic monomers such as alkylene dimethacrylate and alkylene diacrylates and triacrylates. These polymers generally have a molecular weight between 500,000 and 2,000,000. Methylmethacrylate homopolymers and copolymers are preferred. The reactive monomer component may be methyl acrylate or methyl methacrylate although the $C_2$-$C_4$ alkyl(meth)acrylates, such as ethyl(meth)acrylate, propyl(meth)acrylate or (n-, or iso-) butyl(meth)acrylate, can also be used.

These bone cement materials, which are themselves well known and commercially available, are usually provided with 2 parts by weight of the finely divided polymer and 1 part by weight of liquid monomer, although higher or lower ratios can also be used, and are characterized as being self-polymerizable substances which are mixed, together with a polymerization catalyst, such as dibenzoyl peroxide, and polymerization accelerator, such as dimethyl-p-toluidine, immediately prior to the operation to form a viscous liquid or pasty mass.

Curing of the bone cement composition is typically accomplished by any suitable initiator system such as from about 0.1 to about 3% by weight, such as about 0.6% of a conventional free radical initiator. The initiator can be a peroxy compound or an azo compound. For purposes of biocompatability benzoyl peroxide is a very suitable free radical initiator. The curing temperature is generally reduced to room temperature, e.g. about 25° to 30° C., by inclusion in the formulation of an activator for the peroxide catalyst which causes more rapid decomposition of the peroxide to form free radicals. Suitable peroxide catalysts include benzoyl peroxide, 2,4-dichlorobenzoyl peroxide and 4-chlorobenzoyl peroxide. Activators or accelerators for these catalysts include N,N-dialkyl anilines or N,N-dialkyl toluidines generally employed in amounts ranging from about 0.1 to 1% based on the weight of monomer present. A representative activator is N,N-di(2-hydroxyethyl)-p-toluidine. In order to provide longer shelf life for the compositions of the invention, the composition may be stored in a closed container at cold temperature. Stabilizers, such as hydroquinone or chlorophyll may also be added to the monomer compound.

Bone cements containing both activator and peroxide are provided as two-part compositions in which the activator and monomer and peroxide and polymer component may be packaged in separate containers. The proportions by weight of polymer and liquid monomer can range from about 4:1 to 1:2, preferably 3:1 to 1:1.5, such as 2:1, 1.5:1, 1:1 or 1:1.5.

In certain embodiments, the cements may include imaging or "tracer" elements, e.g., radioopaque or radioopacifier elements, which provide for enhanced imaging of the cement during delivery, e.g., as visualized by radiographic imaging techniques. Representative radiopaque particles that may find use include radiopaque materials selected from a group consisting of barium sulfate, zirconium dioxide, tantalum, tungsten, platinum, gold, silver, stainless steel and titanium. Representative tracer elements and protocols for imaging the same are described in U.S. Pat. Nos. 6,309,420 and 6,273,916; the disclosures of which are herein incorporated by reference.

Several representative cements are sold commercially and amenable for use in the subject invention. Such commercially available cements include, but are not limited to: the SIMPLEX™ bone cement (Howmedica-Stryker); the OTEOBOND™ bone cement (Zimmer); the CMW™ bone cement (Depuy); the ENDURANCE™ bone cement (Depuy); and the CORTOSS™ bone cement (Orthovita).

Utility

The subject methods as described above find use in applications where it is desired to use an orthopedic cement that is a material capable of setting up into a solid product when placed at a physiological site of interest, such as in dental, craniomaxillofacial and orthopedic applications, as well as other applications in which a bone defect filling composition is employed. In orthopedic applications, the cement will generally be prepared and introduced to a bone repair site, such as a bone site comprising cancellous bone. The subject methods find particular use in those applications where it is desired to introduce a cement into a cancellous bone target site in a manner such that the cement penetrates the cancellous bone to produce a cancellous bone/cement composite structure.

Representative orthopedic applications in which the invention finds particular use include the treatment of fractures, prosthetic implantaion and/or implant augmentation, in mammalian hosts, particularly humans. In such fracture treatment applications, the fracture may or may not be reduced first, as desired or convenient. Following fracture reduction, if performed, a settable structural material is introduced into the cancellous tissue in the fracture region using the delivery methods described above. Specific dental, craniomaxillofacial and orthopedic indications in which the subject invention finds use include, but are not limited to, those described in U.S. Pat. No. 6,149,655, the disclosure of which is herein incorporated by reference.

One particular representative application in which the subject compositions find use is vertebroplasty, particularly percutaneous vertebroplasty. Percutaneous vertebroplasty is a well-known procedure involving the injection of a bone cement or suitable biomaterial into a vertebral body via percutaneous route under imaging guidance, such as X-ray guidance, typically lateral projection fluoroscopy. The cement is injected as a semi-liquid substance through a needle that has been passed into the vertebral body, generally along a transpedicular or posterolateral approach. The four main indications are benign osteoporotic fractures, malignant metastatic disease, benign tumors of the bone, and prophylactic stabilization of vertebral body. Percutaneous vertebroplasty is intended to provide structural reinforcement of a vertebral body through injection, by a minimally invasive percutaneous approach, of bone cement into the vertebral body. See, for example, Cotton A., et al "Percutaneous vertebroplasty: State of the Art." Radiograhics 1998 Mar-Apr.; 18(2):311-20; discussion at 320-3.

The general steps for performing a vertebroplasty are as follows. The patient is placed in the prone position and the skin overlying the fractured vertebrae is prepped and draped. A suitable local anesthetic such as 1% Lidocaine is injected into the skin underlying fat and into the periosteum of the pedicle to be entered. Next, a skin incision of about five millimeters is made with a No. 11 scalpel blade or other suitable surgical implement. The decision regarding which pedicle to use is made based on CT (computed tomography) and MR (magnetic resonance) images. A needle of an appropriate gauge (such as eleven gauge or thirteen gauge in a smaller vertebral body) is passed down the pedicle until it enters the vertebral body and reaches the junction of the anterior and middle thirds. This area is the region of maximum mechanical moment and usually the area of greatest compression. At this point a vertebrogram can be performed, if desired, by the injection of non-ionic X-ray contrast into the vertebral body to look for epidural draining veins.

Next, a cement is prepared, e.g., according to the methods as described above. The cement is then injected with vibration as described above under lateral X-Ray projection fluoroscopy imaging or other suitable imaging. The posterior aspect of the vertebral body is an important area to observe for posterior extension of cement, and it is generally accepted that this should be watched constantly during the injection. The injection is stopped as the cement starts to extend into some unwanted location such as the disc space or towards the posterior quarter of the vertebral body, where the risk of epidural venous filling and hence spinal cord compression is greatest. The injection is also discontinued if adequate vertebral filling is achieved. On average, about four to five cubic-centimeters of cement can be injected on each side, and it is known to inject up to about eight to ten cubic-centimeters per side.

Systems

Also provided are systems that find use in practicing the methods of the subject invention, as described above. Typically, the subject systems at least include: a cement handling element, e.g., mixing element, delivery element, shaping element, etc.; and a vibratory element for applying a vibratory force to the cement at some point during its preparation and/or use, as described above.

In a representative embodiment, the systems at least include: (a) a delivery device for the cement; and (b) a vibratory element for vibrating the flowable cement composition during delivery. The delivery device in many of these representative embodiments includes a flowable composition introduction element, such as a syringe and needle, where this element is typically attached to a reservoir of the cement composition, e.g., a syringe body filled with the cement.

The vibratory element may be any convenient means for vibrating the cement composition as it is introduced by the delivery device to the target bone site. A representative type of vibratory element that may be included in the subject systems is a device that vibrates a needle or analogous structure of a cement delivery device.

Figure 1:
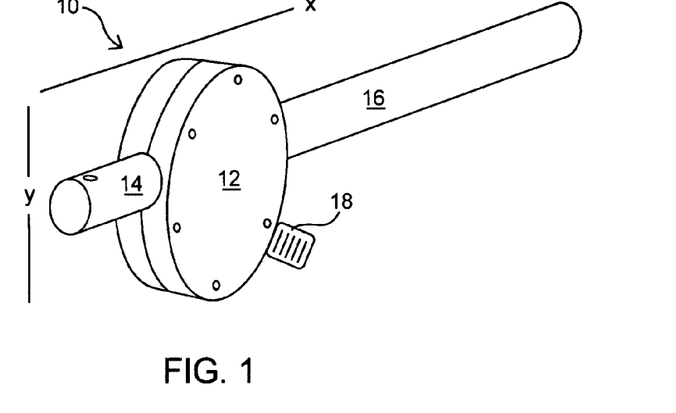

A representative device that is capable of vibrating a needle to deliver a cement to a target site according to the present invention is depicted in various views in FIGS. 1 to 6D. As can be seen in FIG. 1, this representative vibratory element 10 is made up of a pneumatically driven vibrating disc 12 that includes a needle holder 14. When a needle of a cement delivery device (not shown) is present in the needle holder, vibration in the disc is transferred to the needle which, in turn, is transferred to the cement composition being delivered thereby. Also shown is handle 16 (which also serves as an air intake conduit) and exhaust piece 18, through which air leaves the device. The vibratory element is dimensioned for easy use with a cement delivery element, and therefore typically ranges in length X from about 0.25 to 2.5 ft, such as from about 0.5 to about 1.5 feet, including from about 0.75 to about 1 feet; and a height Y ranging from about 0.5 to 12 in, such as from about 1 to about 10 inches, including from about 1 to about 5 inches.

Figure 2:
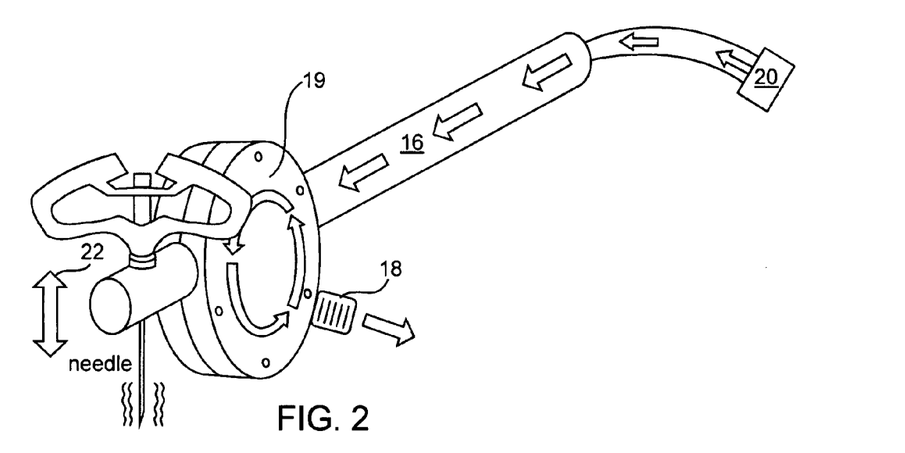

FIG. 2 provides another view of the device shown in FIG. 1, where the air flow through the device is depicted. In the device shown in FIG. 2, airflow generated by an air compressor 20 flows through the handle 16 and into an air intake port of a race or track 19 present inside of the disc. Air flows around the race and out the exhaust 18. Force produced by the air flow propels a steel bearing or ball (not shown) around the track at a high frequency. Momentum of the ball creates up and down vibration in the direction of arrow 22 that is transferred to a needle-holder and ultimately the material being dispensed by the needle. Vibration facilitates the flow of cement by reducing particle adhesion and literally "pushing" the cement downward.

Figure 3:
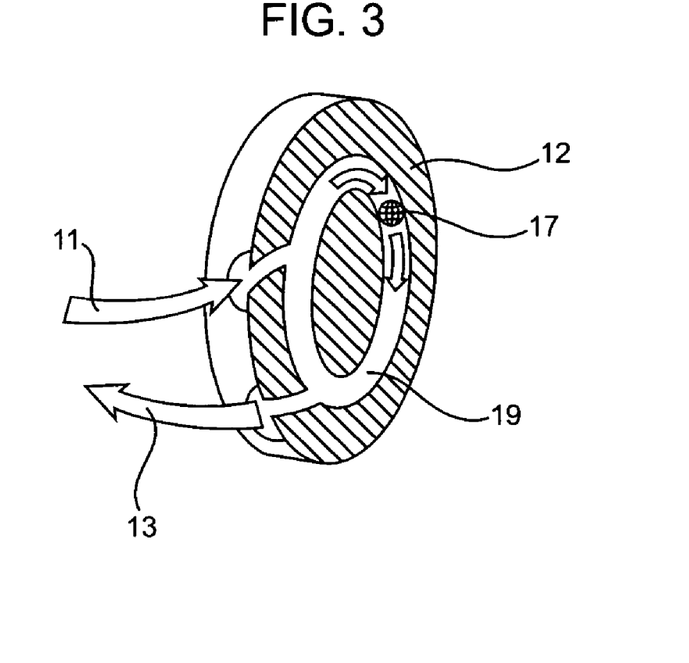

FIG. 3 provides another view of the disc 12 of the device. Shown in the depiction of FIG. 3, disc 12 includes race or track 19 around which ball 17 moves, as driven by air flowing from the intake 11 to the exhaust 13.

Figure 4:
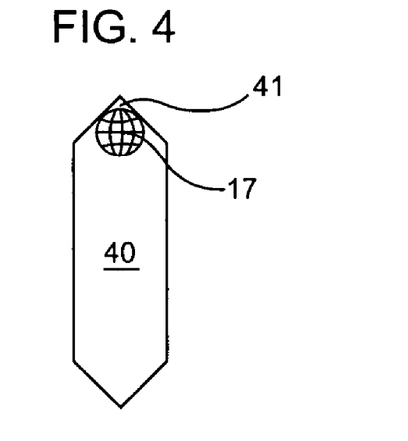

FIG. 4 provides a cross-sectional view of a representative race 40 and a ball 17 inside of the race. The race 40 has an angled end 41 along which the ball travels as it moves along the race.

Figure 5A:
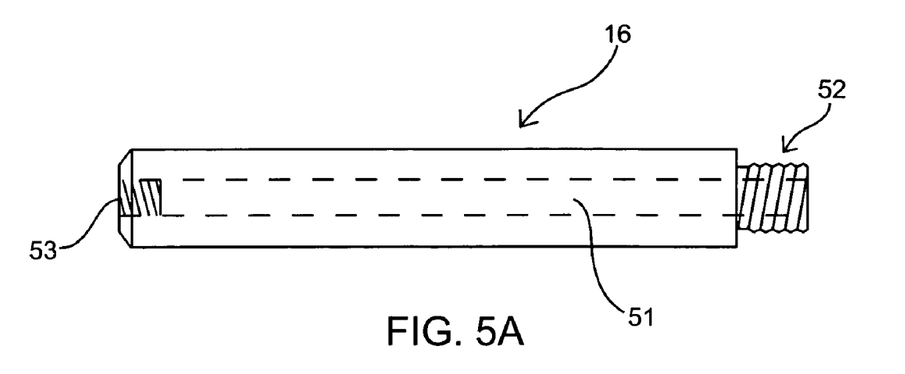
Figure 5B:
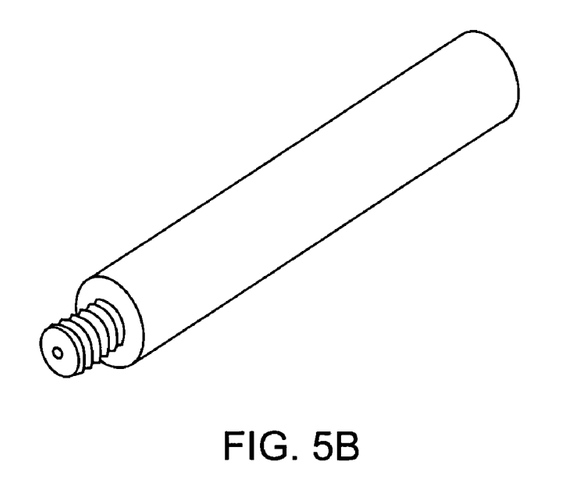

FIGS. 5A and 5B provide detailed views of the handle element 16. As shown in FIG. 5A, handle 16 includes an internal airflow passageway 51 for airflow from an external compressor to the race of the disc component 12. At one of the handle 16 is threaded disc attachment element 52, while at the other end is threaded receiving element 53 for attachment to an external air source, e.g., compressor. FIG. 5B provides an angled view of the handle shown in FIG. 5A.

Figure 6A:
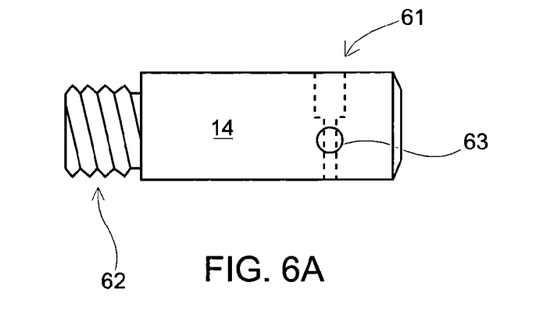
Figure 6B:
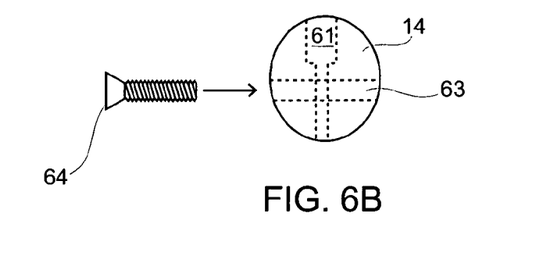
Figure 6C:
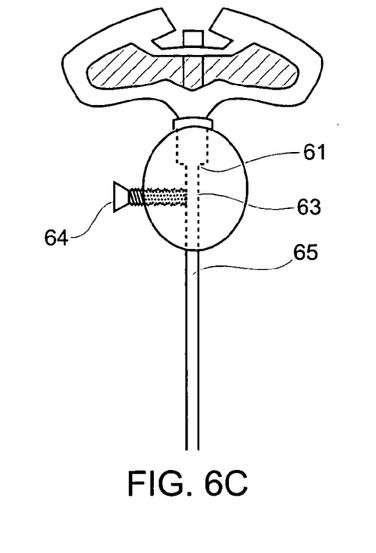
Figure 6D:
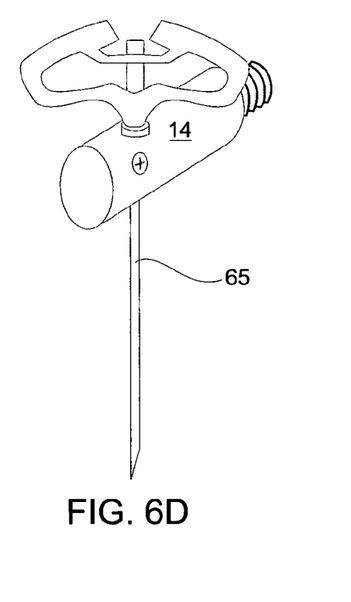

FIGS. 6A to 6D provide various views of needle holder 14. FIG. 6A provides a side view of needle holder 14 showing a through-all hole 61 which is cut and countersunk to fit a delivery needle (not shown). Also shown is threaded disc attachment element 62, and through-all hole 63 for set screw. FIG. 6B provides a front view of the needle 14 showing the through-all hole 63 for the set screw 64, where hole 63 intersects hole 61. FIG. 6C shows a delivery element 65 positioned in hole 61 and held in place by set screw 64 positioned in hole 63. FIG. 6D provides an angled view of needle holder 14 holding a delivery needle 65.

Figure 7:
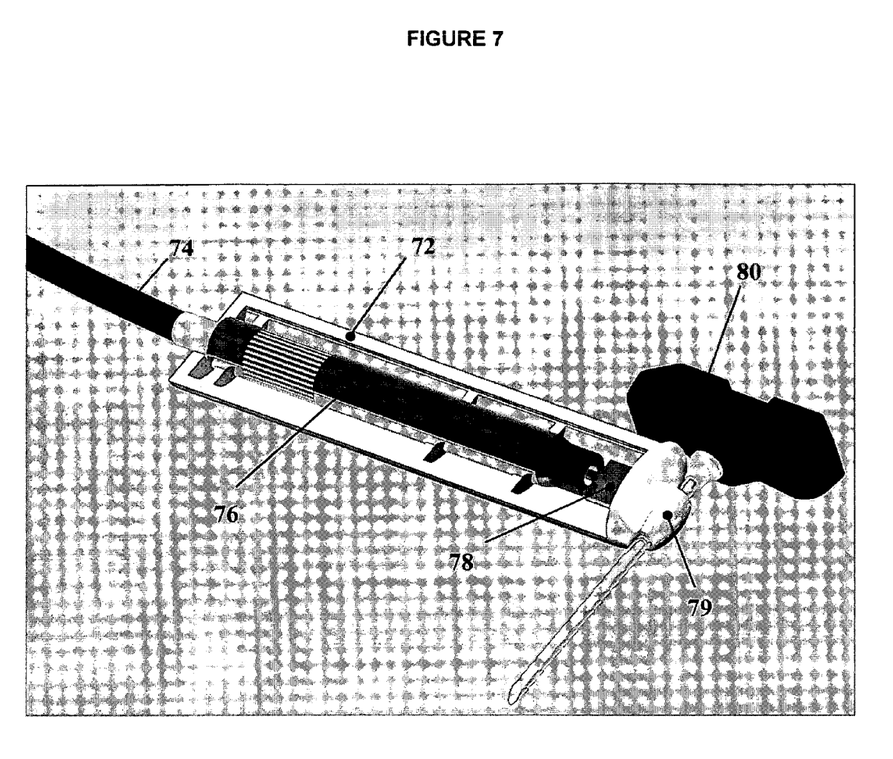
FIG. 7 provides a view of an alternatively pneumatically driven cannula vibrating device that may be employed in certain embodiments of the subject invention.

FIG. 7 provides a view of an alternative vibratory device for imparting vibration to a delivery cannula, and in doing so to a cement being delivered by the cannula. In FIG. 7, device 70 is a hand held device for imparting a vibratory force to a cement delivery cannula. Device 70 includes a housing 72 and compressed air supply 74. Compressed air supply 74 drives Variable RPM air spindle 76. Spindle 76 rotates eccentric mass 78 having a geometry selected to provide for the desired vibratory force. At the distal end of device 70 is cannula interface 79 that interfaces with and holds cannula 80 as shown.

In certain embodiments of the subject systems, the cement delivery device and the vibratory element are distinct from each other, i.e., they are separate devices. In yet other embodiments, the delivery device and vibratory element are found on a single integrated device or instrument.

In certain embodiments, the subject systems further include a cement composition or components thereof, as described above, where the components may or may not be combined into a flowable composition.

Devices

Also provided are cement delivery devices that include a vibratory element which is capable of vibrating a cement composition while it is being delivered, as described above. The vibrating element may be integral or separate from the other components of the device. For example, devices that include a vibrating cement delivery needle, where the vibration of the needle is provided by an element integral to the delivery device, are provided by the subject invention.

Kits

Also provided are kits for use in practicing the subject methods. The kits at least include one or more vibratory elements, as described above, for applying vibration to the cement at some point during it preparation and/or use, e.g., to a component of a delivery device so that a cement delivered by the delivery device can be delivered in accordance with the subject methods. In many embodiments, the kits also include a delivery device for delivering a cement composition, where in certain embodiments the delivery device and vibratory element may integrated into a single instrument, such that they are components of the same device.

In certain embodiments, the kits further include a polymeric cement, where the dry and liquid components may be present in separate containers in the kit, or some of the components may be combined into one container, such as a kit wherein the dry components are present in a first portion and the liquid components are present in a second portion, where the portions are contained so they may or may not be present in a combined configuration, as described in U.S. Pat. No. 6,149,655, the disclosure of which is herein incorporated by reference. As mentioned above, the kit components may be present in separate containers. Alternatively, the components may be present as a packaged element, such as those described above.

In addition to above-mentioned components, the subject kits typically further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

The following examples are offered by way of illustration and not by way of limitation.

EXPERIMENTAL

I. Use of Vibration During Vertebroplasty Using PMMA

An experiment was performed on a cadaver where a PMMA (Polymethlymethacrylate) bone cement (Surgicial SIMPLEX™ bone cement, Howmedica-Stryker) was used as void filler in during vertebroplasty. In this experimental, the device shown in FIG. 7 was attached to the 15 cm long 11-gauge needle of a delivery cannula. The resultant needle/vibrator assembly was inserted through the skin by utilizing transpedicular approach, and the tip of the needle was inserted into the vertebral body. The bone cement material was mixed as instructed in the IFU, and loaded into a 10 cc syringe body. Once the vibrator was turned on, the PMMA bone cement material was delivered into the vertebral body. The pressure of the air tank was adjusted to be 100 psi, and the regulator of the vibrator was set to work within 15 to 30 psi). No pressurization system was used to deliver the material other than finger pressure on the plunger of the syringe. The material was completely delivered within 5 minutes of the start of the injection. The vertebral body was completely filled with PMMA bone cement, as observed by live fluoroscopy as the vibrator was on and applying gentle finger pressure on the plunger. The vibrator was then turned off, and the needle was withdrawn from the surgical site. Three other vertebral bodies were filled with PMMA using the same technique. In each instance, satisfactory PMMA filling of the vertebrae with the above mentioned vibrator device was observed.

For comparison purposes, the vibrator device was then disconnected and PMMA bone cement preparing using the same mixing technique was administered to additional vertebrae in the same patient. Results showed that the amount of fill was not satisfactory as observed with live flouroscopy, and applied pressure on the plunger was more than the previous trials where the vibrator was turned on. It was concluded that the use of vibrator helps the filling of the vertebrae with PMMA, and no pressurization device was necessary during filling of the vertebrae when vibration was employed.

It is evident from the above results and discussion that improved methods (and devices for practicing the same) of using polymeric orthopedic cements are provided. Benefits of the subject methods include improved cement delivery, e.g., delivery which achieves highly controlled penetration of cancellous tissue without the use of high pressure. As such, the subject invention represents a significant contribution to the art.

All publications and patent applications mentioned in this specification are herein incorporated by reference to the same extent as if each individual publication or patent application was specifically and individually indicated to be incorporated by reference.

The invention now being fully described, it will be apparent to one of skill in the art that many changes and modifications can be made thereto without departing from the spirit and scope of the appended claims.

What is claimed is:

1. A method of filling a target bone site with a polymeric bone cement paste composition comprising:
    positioning a holder in a recess of a vibration-generating element;
    introducing a tubular cement composition introduction element through the holder;
    seating the tubular cement composition introduction element in a countersunk recess in the holder;
    positioning at a target bone site an end of the tubular cement composition introduction element that is present in the holder of the vibration-generating element; and
    delivering said polymeric bone cement paste composition through said tubular cement composition introduction element in conjunction with vibration in a manner sufficient to fill said target bone site with said polymeric bone cement paste composition.

2. The method according to claim 1, wherein vibration is also employed in conjunction with preparation of said cement.

3. The method according to claim 1, wherein vibration is also employed in conjunction with preparation of a target bone site for said cement.

4. The method according to claim 1, wherein vibration is also employed in post-delivery modification of said cement.

5. The method according to claim 1, wherein said vibration has a frequency ranging from about 0.1 to about 100,000 Hz.

6. The method according to claim 1, wherein said target bone site comprises a fracture.

7. The method according to claim 1, wherein said target bone site comprises cancellous bone.

8. The method according to claim 7, wherein said vibration provides for controlled penetration of said cement composition into said cancellous bone without use of substantial pressure.

9. The method according to claim 1, wherein said tubular cement composition introduction element is a needle.

10. The method according to claim 1, wherein said tubular cement composition introduction element is a cannula.

* * * * *